US 6,680,073 B1

(12) United States Patent
Tarbet

(10) Patent No.: US 6,680,073 B1
(45) Date of Patent: Jan. 20, 2004

(54) COMPOSITION AND METHOD FOR THE TREATMENT OF ONYCHOMYCOSIS IN ANIMALS

(76) Inventor: Bryon J. Tarbet, 11066 N. 5730 W., Highland, UT (US) 84003

( * ) Notice: Subject to any disclaimer, the term of this patent is extended or adjusted under 35 U.S.C. 154(b) by 0 days.

(21) Appl. No.: 09/545,486

(22) Filed: Apr. 10, 2000

Related U.S. Application Data

(60) Provisional application No. 60/128,604, filed on Apr. 8, 1999.

(51) Int. Cl.[7] ............................................. A01N 59/20
(52) U.S. Cl. ...................... 424/630; 424/405; 424/406; 424/613; 424/616; 424/631; 424/638; 424/642; 424/641; 424/646; 424/648; 514/159; 514/165; 514/731
(58) Field of Search ................................ 424/405–407, 424/78.02, 78.03, 78.05–78.07, 78.09, 613, 616, 622, 630, 631, 638, 78.3, 78.27, 78.19; 514/714, 858, 730, 731–738, 557, 494, 502, 159, 161, 165; 523/122; 534/398, 400

(56) References Cited

U.S. PATENT DOCUMENTS

| | | | | | |
|---|---|---|---|---|---|
| 2,066,363 | A | * | 6/1937 | Patterson | 523/122 |
| 2,457,025 | A | * | 12/1948 | Benignus | 523/122 |
| 2,809,971 | A | * | 10/1957 | Bernstein et al. | 523/122 |
| 3,228,830 | A | * | 1/1966 | McFadden et al. | 523/122 |
| 3,287,210 | A | * | 11/1966 | Leebrick | 523/122 |
| 3,288,674 | A | * | 11/1966 | Yeaser | 523/122 |
| 3,297,525 | A | * | 1/1967 | Grier | 523/122 |
| 5,648,389 | A | * | 7/1997 | Gans et al. | 514/557 |
| 6,099,854 | A | * | 8/2000 | Howard et al. | 424/440 |

* cited by examiner

Primary Examiner—Neil S. Levy
(74) Attorney, Agent, or Firm—Ken H. Tarbet

(57) ABSTRACT

This invention relates to a composition and method for the treatment of white line disease, including ailments such as Onychomycosis, sporotichosis, hoof rot, jungle rot, pseudallecheria boydii, scopulariopsis or athletes foot. The composition of the present invention is useful for the treatment of fungal infections such as Onychomycosis in warm blooded animals such as humans and horses. The method of the present invention is directed to the application of a therapeutic amount of the present composition.

12 Claims, No Drawings

COMPOSITION AND METHOD FOR THE TREATMENT OF ONYCHOMYCOSIS IN ANIMALS

RELATED APPLICATIONS

This application claims the priority filing date of the corresponding Provisional application serial No. 60/128, 604, filed Apr. 8, 1999.

FIELD OF THE INVENTION

This invention relates to a composition and method for the treatment of white line disease, including ailments such as Onychomycosis, sporotichosis, hoof rot, jungle rot, pseudallecheria boydii, scopulariopsis or athletes foot . The composition of the present invention is useful for the treatment of fungal infections such as Onychomycosis in warm blooded animals such as humans and horses. The method of the present invention is directed to the application of a therapeutic amount of the present composition.

BACKGROUND OF THE INVENTION

Maladies such as onychomycosis pose serious health problems including associated problems in dermatology. It has been estimated that the prevalence of onychomycosis in the general population is in the range of 2–13% and increases to about 15–20% in the 40–60 year old age group. Onychomycosis is a condition recognized by discoloration beneath toe nails and finger nails along with pain when pressure is applied near the site of discoloration. The condition usually affects more than one nail. Various fungi, classified as white superficial fungi, cause the condition. Frequently the condition is treated by the combination of nail avulsion and application of a pharmaceutical agent. Presently available topical antifungal formulations for treating onychomycosis have been met with limited success. This is primarily due to the limited ability of such compounds to penetrate into the nail plate, which is hyperkeratotic. The treatment of the condition is further problematic in geriatric patients where therapeutic options are often limited due to possible drug interactions, systemic side effects of treatment, and contraindications secondary to other medical ailments.

The treatment of onychomycosis generally falls into three categories: systemic administration of antifungals; surgical removal of all or part of the nail followed by topical treatment of the exposed tissue; or topical application of conventional creams, lotions, gels or solutions, frequently including the use of bandages to keep these dosage forms in place on the nails. All of these approaches have major drawbacks.

Long term systemic (oral) administration of antifungal agents for the treatment of onychomycosis has been required to produce a therapeutic effect in the nail bed. For example, oral treatment with the antifungal compound ketoconozole typically requires administration of 200 to 400 mg/day for 6 months before any significant therapeutic benefit is realized. Such long term, high dose systemic therapy can have significant adverse effects. For example, ketoconozole has been reported to have liver toxicity effects and reduces testosterone levels in blood due to adverse effects on the testes. Patient compliance is a problem with such long term therapies especially those which involve serious adverse effects.

Accordingly, the risks associated with parenteral treatments generate significant disincentive against their use and considerable patient non-compliance. However, these and other related hinderances to treatment can be potentially avoided by the appropriate use of a therapeutically effective amount of a composition according to the present invention. Moreover the present invention provides a method for the administeration of an effective amount of the present composition comprising the application of the composition to an area in need of treatment and maintaining the composition in contact therewithfor an effetive period of time.

Surgical removal of all or part of the nail followed by topical treatment also has severe drawbacks. The pain and discomfort associated with the surgery and the undesirable cosmetic appearance of the nail or nail bed represent significant problems, particularly for female patients or those more sensitive to physical appearance.

Topical therapy has significant problems too. Topical dosage forms such as creams, lotions, gels etc., do not keep the drug in intimate contact with the nail for prolonged periods of time. Bandages have been used to hold drug reservoirs in place in an attempt to enhance absorption of the pharmaceutical agent. However the bandages are thick, awkward, troublesome and generally lead to poor patient compliance.

Hydrophilic and hydrophobic film forming topical antifungal solutions have also been developed. These dosage forms provide improved contact between the drug and the nail, but the films are not occlusive. Occlusivity is an important factor in increasing drug uptake through the skin and nail. Moreover, topical formulations for onychomycosis treatment have exclusively tried to deliver the drug to the target site (an infected nail bed) by diffusion across or through the nail.

Nail is more like hair than stratum corneum with respect to chemical composition and permeability. Nitrogen is the major component of the nail attesting the to the nail's proteinaceous nature. The total lipid content of mature nail is 0.1–1.0%, while the stratum corneum lipid is about 10% w/w. The nail is 100–200 times thicker than the stratum corneum and has a very high affinity and capacity for binding and retaining antifungal drugs. Consequently little if any drug penetrates through the nail to reach the target site (the nail bed, see FIG. 4, number 16). Because of these reasons topical therapy for onychomycosis has generally been ineffective.

Compounds known as penetration or permeation enhancers are well known in the art to produce an increase in the permeability of skin or other body membranes to a pharmacologically active agent. The increased permeability allows an increase in the rate at which the drug permeates through the skin and enters the blood stream. Penetration enhancers have been successful in overcoming the impermeability of pharmaceutical agents through the skin. However, the thin stratum corneum layer of the skin, which is about 10 to 15 cells thick and is formed naturally by cells migrating toward the skin surface from the basal layer, has been easier to penetrate than nails. Moreover, known penetration enhancers have not proven to be useful in facilitating drug migration through the nail tissue.

Antimicrobial compositions for controlling bacterial and fungal infections comprising a metal chelate of 8-hydroxyquinoline and an alkyl benzene sulfonic acid have been shown to be efficacious due to the increased ability of the oleophilic group to penetrate the lipoid layers of microcells. The compounds however, do not effectively increase the ability to carry the pharmaceutically active antifungal through the cornified layer or stratum corneum of the skin. U.S. Pat. No. 4,602,011, West et al., Jul. 22, 1986; U.S. Pat. No. 4,766,113, West et al., Aug. 23, 1988.

The composition of the present invention is directed a method and composition for treating onychomychosis, and related infections, in animals. Because onychomychosis is an infection afflicting all animals with a nail or hoof, this composition is useful in the treatment of any animal with a nail or hoof.

Onychomychosis is a fungal infection of the nail or hoof bed. Because the infection is under the nail or hoof it is dificult to treat. Traditional methods of treatment involve complete nail removal. Not infrequently the chosen treatment regime involves nail removal combined with topical treatment of the now exposed infected tissue. However, the removal of an infected hoof requires complete imobilization of the animal, an often impossible task. This treatment regime is therefore unreasonable for the treatment of hoofed animals, such as horses.

Topical treatments have also been imployed. However because the nail is largely impervious to the transfer of drugs, little of the applied drug reaches the infected tissue. This problem is more pronounced in hoofed animals where the nail is many time thicker than the nail of a human.

However if white line disease is allowed to grow unchecked, it can result in the crippling of the animal. The unchecked growth of the fungus in humans often inflicts substantial pain. In humans afflicted with onychomycosis is often subjected to both physical and emotional pain.

The inventor has solved the problem of treating a human afflicted with onychomychosis, without surgery. Moreover, the present invention solves this long felt need through the formulation of a composition which has unique properties relative to migration into the infected site.

It would therefore be useful to provide a composition for the treatment of onychomychosis and related infections in animals.

It would further be useful to provide a method for the administeration of the present composition for the treatment of onychomychosis in animals.

DESCRIPTION OF THE INVENTION

These and related problems are addressed through a method of treatment of an infected nail or hoof which method may involve the composition according to this invention. The composition to be applied to the infected nail/hoof comprising:

a salicylate, including aids, esters, amides and salts, the salicylate having the general structure (I).

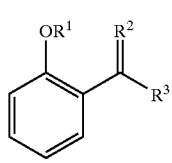

(I)

where $R^1$ is hydrogen, alkyl, hetero, heteroalkyl, aryl or heteroaryl;

$R^2$ and $R^3$ are independently alkyl, hetero, heteroalkyl, aryl or heteroaryl;

At least one copper species such as a Cu (II) and/or Cu(I), as a salt such as $CuSO_4$ or $CuNO_3$ for example, a complex such as copper glycinate for example or a chelate such as copper-$(glycine)_2$.

An organic or inorganic peroxide, or both an organic and an inorganic peroxide, including a composition which becomes a peroxide in situ.

A polyhydroxy aromatic, which has at between: about 1–6 hydroxy moieties if the aromatic is monocyclic, and between about 1–4 hydroxy moieties for each aromatic ring on a polycyclic aromatic, hydroxy and polyhydroxy aromatics.

The elements Co, Zn, Fe in any of their stable cationic forms. Moreover, the cations may be included as ionic salts, organic salts or chelates or as part of a complex.

The above components are admixed in a hydrophyllic composition comprising:

between about 50–99% by weight water and 1–50% by weight alcohol, such as alkyl-OH, and between about 1–50% by weight $C_1$–$C_{10}$ mono or polyhydroxy oxyalkane according to formula (II).

(II)

Co in in a complex such as in $B^{12}$

Furthermore the composition may optionally include boric acid, borates, poly dimethyl ammonium tetramethyl diamine (ethylene diamine bis-epoxy) polymer, also known as poly DADMAC, including peroxy combinations of the salicylates, borates.

DEFINITIONS OF TERMS

Whiteline, white line and onycomycosis are used herein interchangable for an infection around and/or in or near the nail or hoof.

Alkyl shall mean a hydrocarbon chain of between 2 to about 25 carbons of either branched or straight alkyl chain and either fully saturated or containing between 1 and about 10 unsaturation bonds.

Heteroatom shall mean a heteroatom such as N, O, S or P.

Heteroalkyl shall mean an organic moiety containing both a heteroatom and an alkyl portion.

Hydrophylic carrier shell mean a composition which is water disperseable, may contain water, an organic alcohol with between 1 to 10 carbons, and has essentially the formula HO-Alkyl.

Debridement shall have the definition as contained in Webster's Dictionary as published by Simon and Schuster.

EXAMPLES

Example 1

The treatment solution was prepared by adding about 100–300 grams of salicylic acid to 4 Liters of warm water. This was followed by 10–100 g NaOH and 1–60 grams of boric acid. The solution was mixed and filtered to remove traces of undissolved material. Then about 1–100 grams of copper sulfate were added and the solution became a light green. The solution was allowed to cool and 1–100 mL of hydrogen peroxide was added. Finally, the solution was diluted to 20 L with water.

Example 2

The treatment solution was prepared by adding about 230 grams of salicylic acid to 4 Liters of no warm water. This was followed by 45 g NaOH and 25 grams of boric acid. The solution was mixed and filtered to remove traces of undissolved material. Then 10 grams of copper sulfate were added and the solution became a light green. The solution was allowed to cool and 1–100 mL of hydrogen peroxide was added. Finally, the solution was diluted to 20 L with water.

Example 3

The treatment solution was prepared by adding about 230 grams of salicylic acid to 4 Liters of warm water. This was followed by 45 g NaOH and 25 grams of boric acid. The solution was mixed and filtered to remove traces of undissolved material. Then 50 grams of copper sulfate were added and the solution became a light green. The solution was allowed to cool and was packaged. Finally, the solution was diluted to 20 L with water.

What is claimed is:

1. A composition for the treatment of an animal afflicted with onycomychosis, the composition comprising:

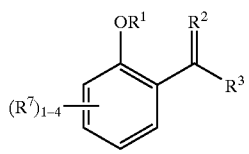
(I)

where $R^1$ is hydrogen;

$R^3$ is hydroxy;

$R^2$ is hetero, and each $R^7$ is independently hydrogen;

a copper composition;

a peroxide;

a polyhydroxy aromatic compound;

a transition metal coordination complex, all dissolved in water, wherein the composition contains greater than 100 mg copper composition.

2. The composition according to claim 1 wherein, $R^2$ is oxygen.

3. The composition according to claim 2 wherein the copper composition is a copper complex.

4. The composition according to claim 3 wherein the copper complex is a diamine polymer-copper complex.

5. The composition according to claim 1 wherein the coordination complex is a Co chelate or complex.

6. The composition according to claim 1 wherein the coordination complex is a Zn chelate or complex.

7. The composition according to claim 1 wherein the coordination complex is a Fe chelate or complex.

8. The composition according to claim 1 wherein the polyhydroxy aromatic compound is 1,2,4,5-tetra hydroxy benzene.

9. The composition according to claim 1 wherein the peroxide is an organic peroxide.

10. The composition according to claim 1 wherein the peroxide is an inorganic peroxide.

11. The composition according to claim 1 wherein the peroxide is hydrogen peroxide.

12. A pharmaceutical composition for the topical treatment of onychomycosis comprising composition according to claim 1 and a pharmaceutically acceptable carrier.

* * * * *